United States Patent
Carper et al.

(10) Patent No.: US 11,071,828 B2
(45) Date of Patent: Jul. 27, 2021

(54) COLORED SEAL SYSTEM, METHOD, AND APPARATUS

(71) Applicant: Treble Innovations, LLC, Spanish Fork, UT (US)

(72) Inventors: Scott Carper, Freeburg, PA (US); Brian Dean Owens, Plano, TX (US); Roland Clifford Park, Springville, UT (US)

(73) Assignee: Treble Innovations, LLC, Spanish Fork, UT (US)

( * ) Notice: Subject to any disclaimer, the term of this patent is extended or adjusted under 35 U.S.C. 154(b) by 211 days.

(21) Appl. No.: 16/257,891

(22) Filed: Jan. 25, 2019

(65) Prior Publication Data

US 2019/0231983 A1 Aug. 1, 2019

Related U.S. Application Data

(60) Provisional application No. 62/622,279, filed on Jan. 26, 2018.

(51) Int. Cl.
*A61M 5/31* (2006.01)
*A61M 5/315* (2006.01)

(52) U.S. Cl.
CPC ...... *A61M 5/3129* (2013.01); *A61M 5/31525* (2013.01); *A61M 5/31556* (2013.01); *A61M 5/31511* (2013.01); *A61M 2005/3125* (2013.01); *A61M 2205/583* (2013.01); *A61M 2205/6081* (2013.01)

(58) Field of Classification Search
CPC ............ A61M 5/3129; A61M 5/31525; A61M 5/31556; A61M 2205/6081; A61M 2005/3125; A61M 2205/583; A61M 5/31511
See application file for complete search history.

(56) References Cited

U.S. PATENT DOCUMENTS

| | | | |
|---|---|---|---|
| 4,452,251 A * | 6/1984 | Heilman | A61M 5/3129 116/227 |
| 5,242,405 A | 9/1993 | Howe | |
| 6,290,678 B1 | 9/2001 | Aydelotte et al. | |
| 2005/0080384 A1 | 4/2005 | Green | |
| 2013/0310760 A1* | 11/2013 | Ivosevic | A61M 5/3129 604/207 |

(Continued)

FOREIGN PATENT DOCUMENTS

WO 2007014428 A1 2/2007

OTHER PUBLICATIONS

"Correspond", https://www.merriam-webster.com/dictionary/correspond (Year: 2020).*

*Primary Examiner* — Theodore J Stigell
*Assistant Examiner* — Rachel T. Smith
(74) *Attorney, Agent, or Firm* — Goodhue, Coleman & Owens, P.C.

(57) ABSTRACT

A colored seal system, method, and apparatus. The colored seal system includes a barrel having a delivery end and an open end. The barrel includes multiple markings. The barrel markings include at least measurements and multiple fill indicators. The colored seal system includes a colored seal slidably positioned within the barrel for moving a delivery agent. The colored seal is visible within at least one of the fill indicators.

24 Claims, 7 Drawing Sheets

(56) References Cited

U.S. PATENT DOCUMENTS

2014/0207073 A1\* 7/2014 Shang ............... A61M 5/31566
 604/189
2014/0207079 A1\* 7/2014 Creaturo ............. A61M 5/3129
 604/207

\* cited by examiner

COLORED SEAL SYSTEM, METHOD, AND APPARATUS

RELATED APPLICATION

This application claims priority to U.S. Provisional Patent Application No. 62/622,279 entitled "Colored Seal System, Method, and Apparatus" Jan. 26, 2018, hereby incorporated by reference in its entirety.

BACKGROUND

I. Field of the Disclosure

The illustrative embodiments relate to dosing equipment. More specifically, but not exclusively, the illustrative embodiments relate to a system, method, and apparatus for utilizing colored seals and barrel markings for measuring and distributing medicines and other fluids.

II. Description of the Art

The overall population grown throughout the world has similarly increased the amount of medicines that are prescribed and otherwise used by individuals. Current syringes, needles, or other systems and apparatus for distributing medicines, fluids, or other content are often hard to read or decipher. This is particularly true for those with poor eyesight, physical or mental impairments, elderly/young users, low light conditions, and other similar environments or personal conditions. As a result, measurements, dosing, and other forms of delivery are often performed improperly (e.g., too much or too little medicine) resulting in deaths, injuries, lawsuits, improper healing, wasted time, and other undesired outcomes.

SUMMARY OF THE DISCLOSURE

A colored seal system, method, and apparatus is provided. The colored seal system includes a barrel having a delivery end and an open end. The barrel includes multiple markings. The barrel markings include at least measurements and a plurality of fill indicators. The colored seal system includes a colored seal slidably positioned within the barrel for moving a delivery agent. The colored seal is visible within at least one of the fill indicators.

Another embodiment provides a syringe. The syringe includes a barrel including a needle at a first end and multiple barrel markings. The barrel markings include at least measurements and multiple fill indicators. The syringe includes a colored seal slidably positioned within the barrel for moving a delivery agent within the barrel. The colored seal is fluorescent is visible within at least one of the fill indicators when so positioned.

Another embodiment provides a dosing system. The dosing systems includes a barrel including a delivery end and a plunger end. The barrel includes barrel markings, the barrel markings include at least measurements including line markings and volumetric markings and fill indicators associated with at least the volumetric markings. The dosing systems includes a colored seal slidably secured within the barrel for communicating a delivery agent within the barrel. The colored seal is fluorescent visible within at least one of the fill indicators when aligned. The dosing system includes a plunger connected to the colored seal for receiving a user force to add or eject the delivery agent from the barrel.

Another embodiment provides a method for utilizing a dosing system. The dosing system connects to a reservoir for drawing a delivery agent. A plunger is retracted to move a colored seal within a barrel of the dosing system. The colored seal is aligned so that the colored seal is visible within one or more fill indicators on the barrel. The fill indicators are associated with measurements on the barrel.

In some alternative embodiments, the colored seal is connected to a plunger or plunger rod for moving the colored seal within the barrel to insert and remove the delivery agent. The barrel may be transparent or semi transparent with the colored seal being fluorescent. The measurements may include line markings and numeric markings. The fill indicators may correspond to fill levels for the numeric markings. The fill indicators may represent hollow or outline shapes. The fill indicators may be circles, squares, triangles, ovals, stars, octagons, hexagons, rectangles, or other shapes or symbols. A size of the front bevel of the colored seal within the barrel may correspond to a size of the fill indicators. The measurements for the delivery agent may be associated with a position of the fill indicators to compensate for the size and shape of the colored seal. A front end of the colored seal may be aligned with one of the fill indicators such that a color of the colored seal is visible within the fill indicator and one of the fill indicators is associated with one of the measurements. The fill indicators represent a pair of lines extending all or a portion of a circumference of the barrel. A separation of a pair of lines may be associated with a width of a front bevel (nearest the delivery agent) of the colored seal within the barrel. The fill indicators may be filled with a second color. A new color may be visible when the colored seal is aligned with the second color of the fill indicators. The barrel markings may be black or other colors. The delivery end of the syringe includes one of a needle, connector, discharge hole, or a tube.

BRIEF DESCRIPTION OF THE DRAWINGS

Illustrated embodiments are described in detail below with reference to the attached drawing figures, which are incorporated by reference herein, and where.

DETAILED DESCRIPTION OF THE DISCLOSURE

Figure 1:
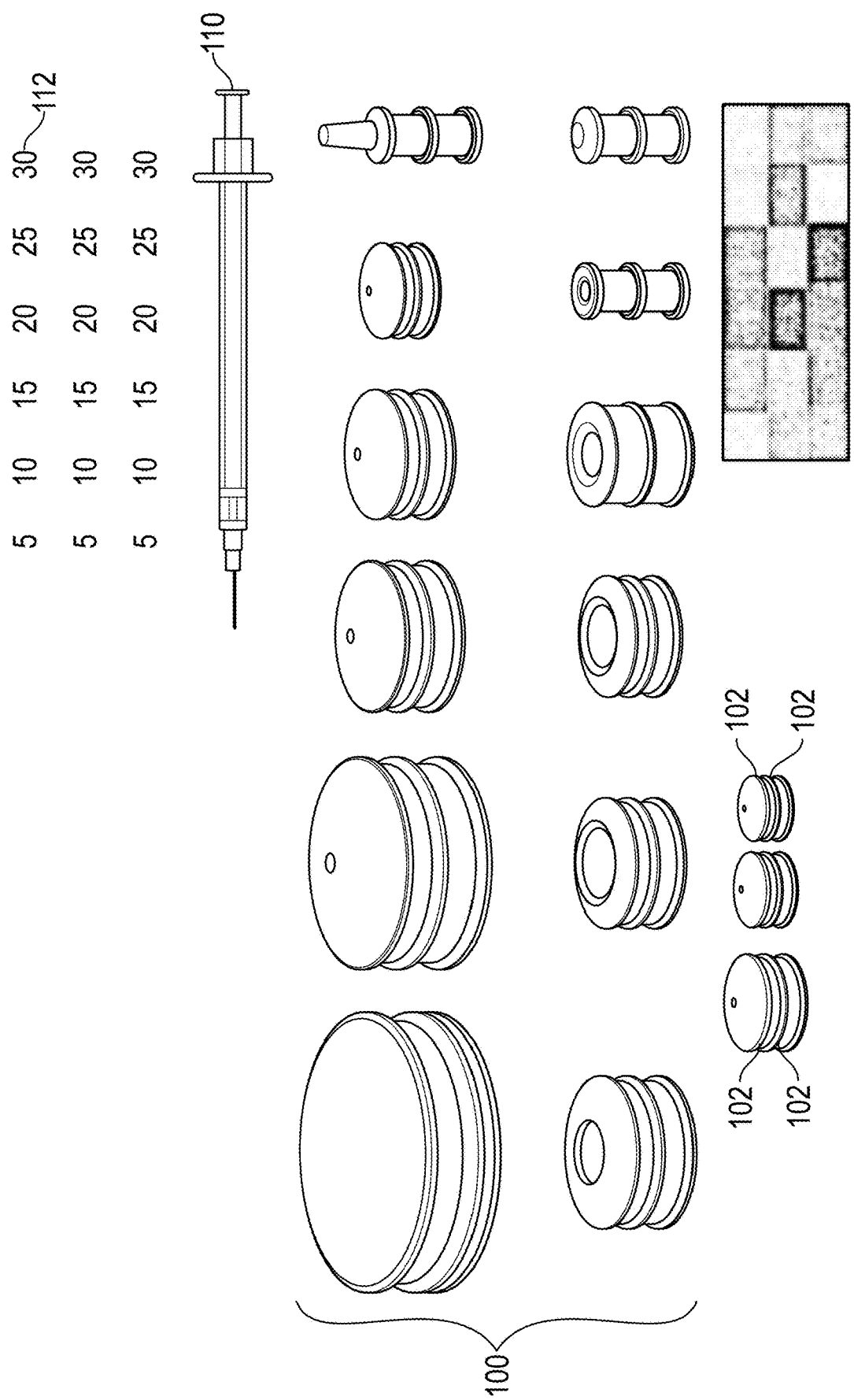
FIG. 1 is a pictorial representation of various colored seals in accordance with an illustrative embodiment.

The illustrative embodiments provide a system, method, and apparatus that utilize various unique combinations to ensure the proper measurement and delivery of fluids, medicines, solids, or other delivery agents. The delivery agents may be distributed for the benefit of individual users, patients, animals, experiments, mixtures, or chemical, medical, business, or manufacturing processes. For purposes of simplicity, a person, animal, material, device, receiving party, or process that utilize the illustrative embodiments are referred to herein as a user. A user, animal, experiment, or process that receives the delivery agent may also be referred to herein as a receiving user (or user). The illustrative embodiments may utilize neon, fluorescent, or colored seals that gather and reflect more light for enhanced visibility. The seals may also be glow-in-the-dark or luminescent. The seals may also be motion or user activated utilizing a light and battery (e.g., watch battery, LED, etc.) or chemically activated (e.g., contact with a liquid activates luminescence). As a result, the seals are inherently more visible to the human eye than standard black seals that are utilized in needle systems, plungers, or analogous systems. The colored seals may also be referred to as a colored piston. The colored seal and a plunger may be integrated, attached, or independent.

The seals move within one or more barrels, containers, syringes, or receptacles. For example, the seals may provide a watertight seal within the barrel of a syringe when drawing and injecting a delivery agent. The seals are utilized at one or more ends or points along a plunger or similar component. The seals ensure that the delivered agents are effectively moved and communicated through a structure to a delivery end, such as a needle, tube, connector, opening, catheter, or so forth, for immediate or subsequent delivery to a user. The colored seals may include one, two, three or more bevels. The size and shape of the bevels may vary. The bevels may alternatively be referred to as rings. In one embodiment, the colored seal includes two seals for ensuring the efficient movement and delivery of the delivery agent. For example, the colored seals provide a watertight/airtight seal within the barrel of the syringe or delivery system for drawing and injecting the associated delivery agent. The portion of the colored seal closest to the delivery end including the bevel, edge, or ring within the barrel may be utilized to measure the delivery agent.

The barrel is in large part clear, transparent, semi-transparent or so forth for an individual to view the delivery agent within the barrel as measured, loaded, pre-loaded, drawn, or otherwise made available. The barrel may also have a transparent window for viewing movement of the colored seal when loading/drawing or discharging/delivering the delivery agent. In one embodiment, the barrel or other object in which the colored seal moves the delivery agent includes fill indicators. The barrel may include an integrated or separately connected flange for better manipulating the barrel within the hand of the user. For example, the flange may be utilized to draw a fluid (e.g., medicine, liquid, delivery agent, etc.) or solid.

In one embodiment, the fill indicators are black or dark markings and indicators. Other different colors or combinations may also be utilized for the fill indicators. For example, the colored seal and the fill indicators may visibly interact to provide distinctions for the user (e.g., brighter colors, different color combinations, etc.). The fill indicators may represent line markings or shapes that are unfilled (e.g., transparent, open, not solid, line shapes, etc.) or hollow so that the color of the colored seal is visible within or through the fill indicators. The fill indicators may be printed, deposited, rolled, painted, engraved, embedded, or otherwise positioned on or integrated with the barrel. In one embodiment, the fill indicators correspond to measurement intervals or points along the barrel associated with the delivery capacity for the delivery agent (e.g., 0.5 mL, 1 mL, 5 mL, 10 mL, 100 mL, etc.). The alphanumeric text markings on the barrel may also be referred to as numeric markings. In one embodiment, one or more of the fill indicators are completely filled (or appears to be filled) by the color associated with the colored seal at one or more designated measurements. For example, the fill indicator may be one or more of a shape (e.g., circle, square, pair of lines, etc.), numbers (e.g., volume, content measurement, etc.), text, objects, or other demarcations. In one embodiment, the size of the fill indicator is associated with a bevel of the seal to ensure proper measurements. For example, the width or diameter of the fill indicators may correspond to a width of the bevel. The width of the bevel may be size with the inside width of the fill indicators or hollow, blank, or open space defined by the fill indicators. A first side of the fill indicator may also be positioned, such that when the seal is moved a measurement amount is exactly reached when the colored seal appears to fill the fill indicator. In one embodiment, the width of the fill indicator may exactly correspond to the width of the bevel(s) of the colored seal. As a result, once the bevel appears within the fill indicator, the desired measurement has been reached.

In another embodiment, the bevel(s) of the colored seal may utilize a distinct color from the rest of the colored seal to indicate that a desired measurement has been reached. For example, the bevels of the colored seals may be differently colored. In one embodiment, the bevels may be colored utilizing printing, rolling, deposition, manufacturing, or so forth. The bevels may be colored during manufacturing or generation or after being generated. Shapes, lines, numbers, or other objects may also be present on or integrated with the colored seal to be visible in the fill indicators. The fill indicators may be automatically or manually filled with the colored seal to determine an associated measurement has been reached.

In another embodiment, the fill indicators are filled with a first color that appears as a third color when the second color associated with the colored seal is properly aligned. The distinct or third color created by the color combinations of the first color of the fill indicators and the second color of the colored seal indicate that a specified fill point or measurement has been reached. In most embodiments, the barrel may include multiple fill indicators associated with text markings or numeric markings along the barrel.

The colored seal may utilize one, two, or multiple colors that provide different indicators and demarcation points. In another embodiment, the seals may include colored bands, rings, washers, bevels, or other components that are integrated with or attached around the seals. The colored portions of the seals act as demarcation points or indicators (see for example bevels 202 of FIG. 1). The colored seals as referenced herein may also be referred to as colored stoppers, stoppers, and/or plunger tips.

As is known, the syringe may be a simple reciprocating pump including a plunger/piston (or plunger rod) that fits tightly within a cylindrical tube called a barrel. The plunger rod may include a thumb press where a user may press to push the plunger rod down into the barrel to expel the delivery agent. One or more seals or stoppers ensure the tight or waterproof fit between the barrel and the plunger/piston. The seals prevent the delivery agent from leaking or escaping around the plunger. The seal also acts as an indicator for measuring the contents of the delivery agent within the barrel. For example, measurements may be made to a topmost portion of the seal that abuts the edges of the barrel (and not the overall topmost portion of the seal with pointed, rounded, or other shaped seals). The barrel may be a reservoir holding the delivery agent and may be clearly graduated to allow accurate and visual measurement of the contents within the barrel. The barrel may include or define flanges or wings that extend from the sides of the syringe barrel to provide an area or surface for the fingers (e.g., index finger and middle finger) to grasp during aspiration or administration. The plunger may be linearly pushed and pulled along the inside of the barrel allowing the syringe to take in and expel liquid, gasses, or solids (i.e., delivery agents) through a discharge orifice at the front or open end of the barrel. The barrel may include scale markings indicating the amount or volume (e.g., milliliter mL/cc, units, etc.) of the delivery agent. The open end of the syringe may be fitted with or include a hypodermic needle, a nozzle, tube, or other connectors to direct the flow into and out of the barrel. The syringes as described herein may commonly be used for administering injections, infusing intravenous therapy, applying or measuring compounds, and/or drawing or measuring a delivery agent.

The above provided description is applicable to all of the embodiments in each and every Figure. In addition, Applicants intend for the different embodiments, components, functions, and aspects of the description and Figures to be combined without restriction whether or not artificially imposed or required. Combinations, variations, and substitutions of the content, description, functionality, potential variations, and embodiments in each of the Figures is expected, contemplated, and applicable across all of the Figures. For example, combinations of the colors, colored seals, measurements/markings, fill indicators, are both expected and required.

FIG. 1 is a pictorial representation of various colored seals 100 in accordance with an illustrative embodiment. As described herein, the colored seals 100 may be referred to collectively or as an individual colored seal 100 or colored seals 100. In one embodiment, the colored seals 100 are indicative of various embodiments of colored seals 100 that may be utilized in the described embodiments. As shown, the color, diameter, size, shape, bevels, and other attributes of the colored seals 100 may vary extensively. The colored seals 100 may be utilized in a syringe 110. The size of the syringe 110 and corresponding barrel, plunger rod, flange, thumb rest, needle/connectors/injection end, and other components may vary significantly. Similarly, the number and type of fill indicators, numeric markings 112, and line markings may vary as is subsequently shown and discussed. The numeric markings 112 may correspond to the size, shape, and measurement units of the syringe 110 with different sizes and styles of font being utilized. In one embodiment, outline or hollow numbers may be particularly effective for viewing the numeric markings 112 when aligned with the colored seals 100.

In one embodiment, the colored seals 100 are connectably or slidably attached to a plunger (or other connector, link) that is utilized to move the seals within a barrel (or other structure, repository, container, etc.). Although shown as black for purposes of simplicity, the colored seals 100 may represent any number of highly visible colors, such as neon or fluorescent yellow, pink, red, green, orange, purple, blue, or other similar color combinations (as are shown in subsequent Figures). In one embodiment, the colored seals 100 may represent fluorescent, neon, luminescent, or other bright colors. Innumerable color variations are known and expected, such as Purple/fuchsia HEX FF00FF/RGB 255, 0, 255; Neon Green HEX 39FF14/RGB 57 255 20; Fluorescent Yellow HEX FFFD01/RGB 255, 253, 1; Fluorescent Pink HEX FF1493/RGB 255, 20, 147; Orange HEX FF8300/RGB 255,131,0; Blue HEX 228DFF/RGB 34, 141, 255, Fluorescent Red HEX fe0000/RGB 254,0,0, white, or lighter or darker variations of the colors or other colors that are substantially similar. For example, a very important color yellow-green may correspond to the wavelength of 555 nm. The colored seals 100 represent these different colors even if not correspondingly shown in the Figures. In one embodiment, the colored seals 100 may be composed of a material or combination of materials that represent the highly visible colors. In another embodiment, the colored seals 100 may have the colorant coated, painted, chemically altered, optically altered, electrically deposited, or so forth.

Colors that have a high contrast may also be used for the colored seals 100. For example, white seals with black indicators/markings on the barrel may be utilized or yellow seals with blue indicators/markings on the barrel or any number of high contrast combinations.

In some embodiments, bevels 102 of the colored seals 100 may be differently colored from the rest of the colored seals 100. All or portions of the bevels may be differently colored. For example, the bevels 102 may be a first color and the rest of the colored seals 100 may be a different color (e.g., black and fluorescent green, fluorescent yellow and fluorescent red, etc.).

Figure 2:
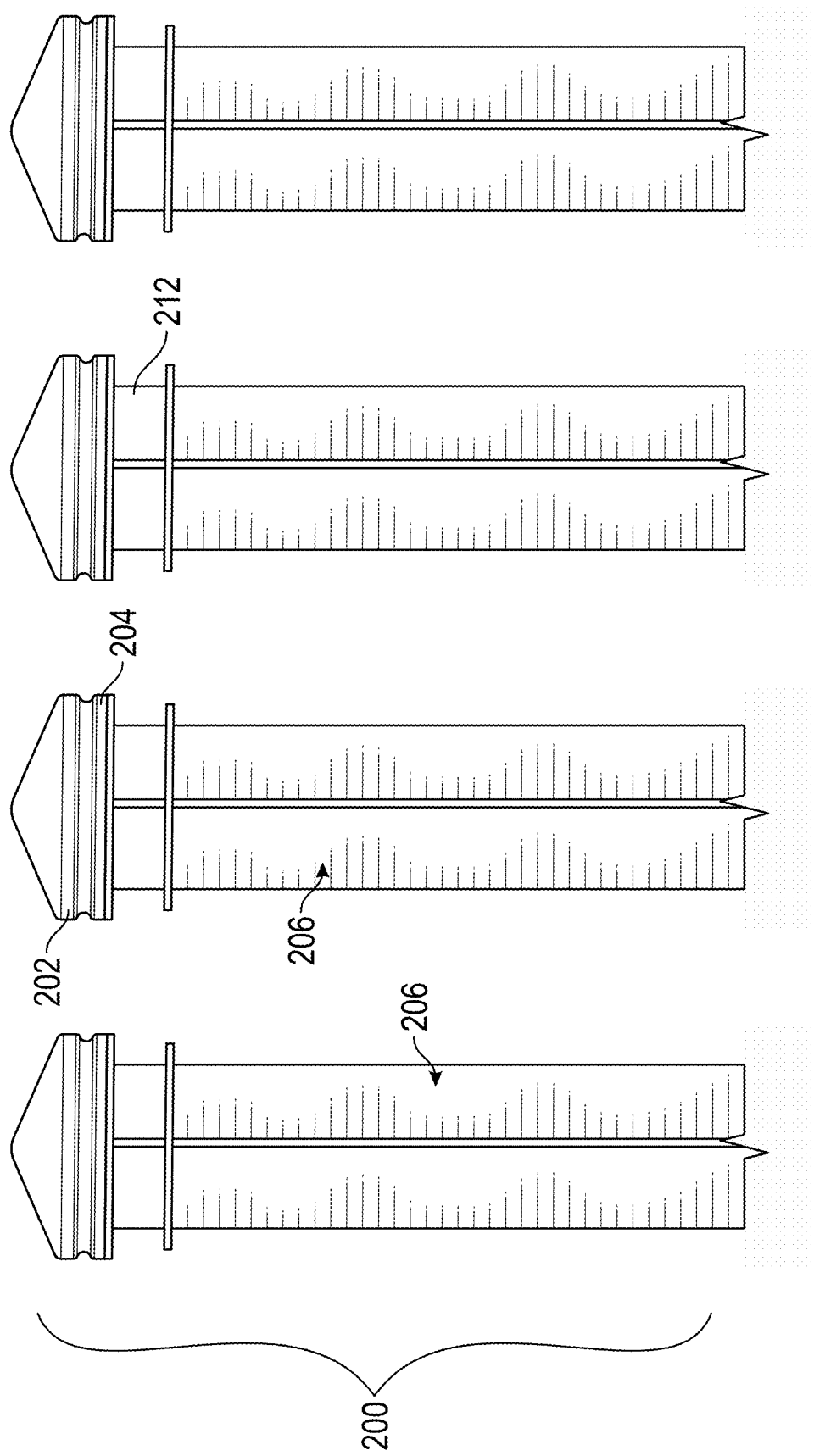
FIG. 2 is a first side view of colored seals in accordance with an illustrative embodiment.
Figure 3:
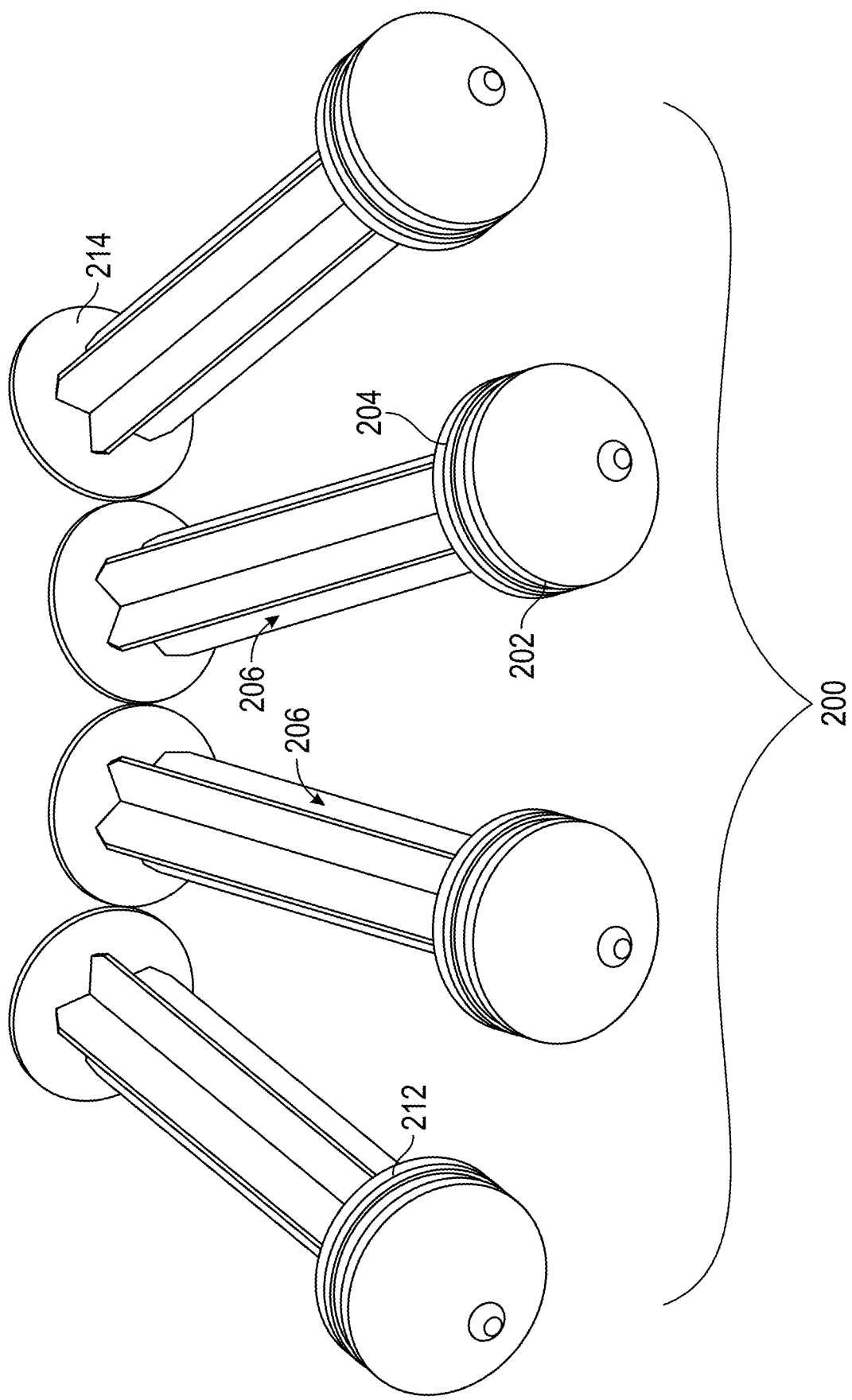
FIG. 3 is a pictorial representation of the colored seals of FIG. 2 in accordance with an illustrative embodiment.
Figure 4A:
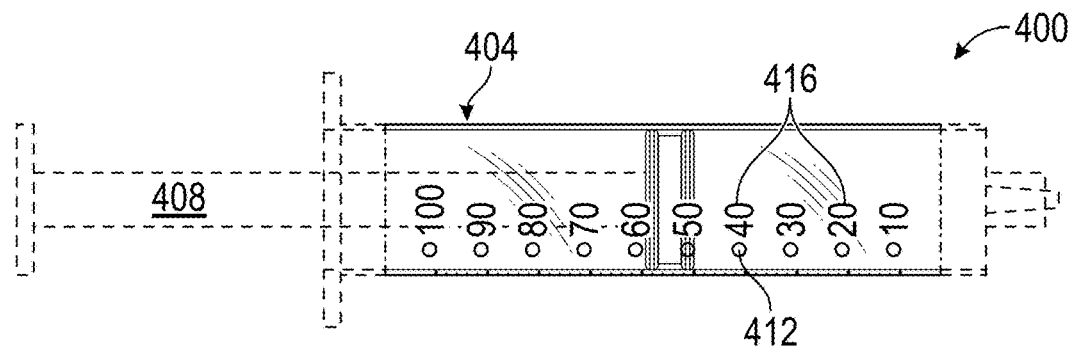
FIGS. 4A-4E illustrate pictorial representations of a syringe in accordance with an illustrative embodiment.
Figure 4B:
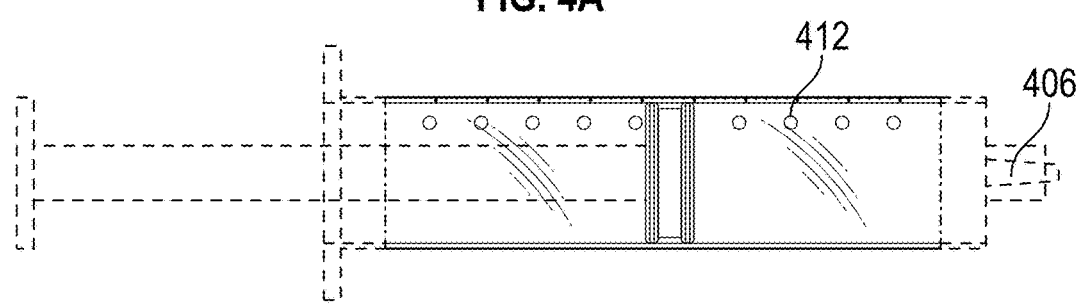
Figure 4C:
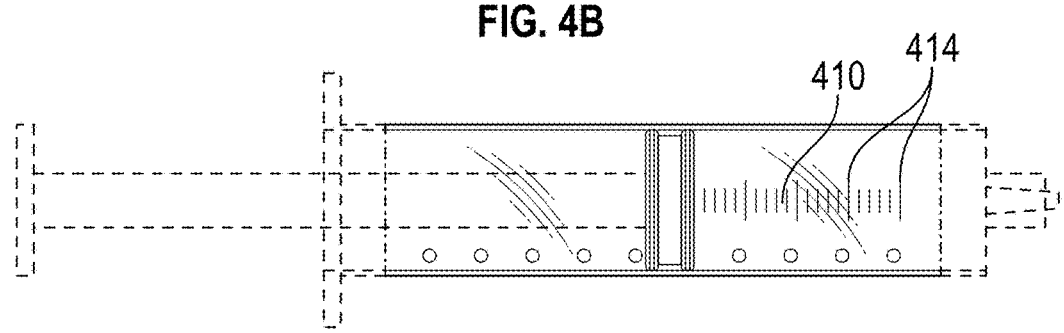
Figure 4D:
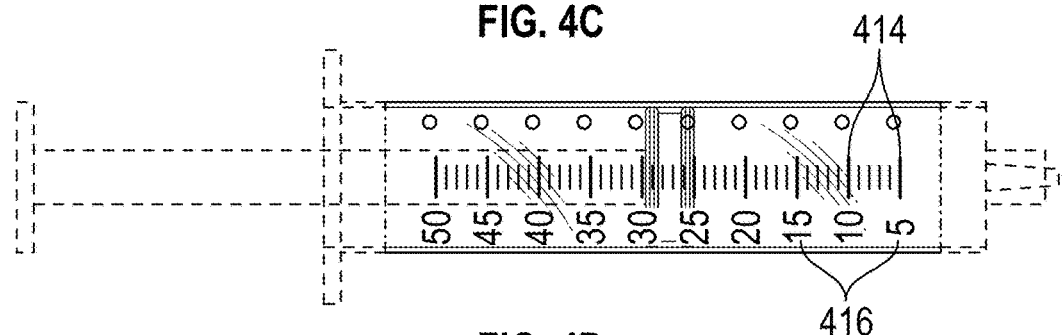
Figure 4E:
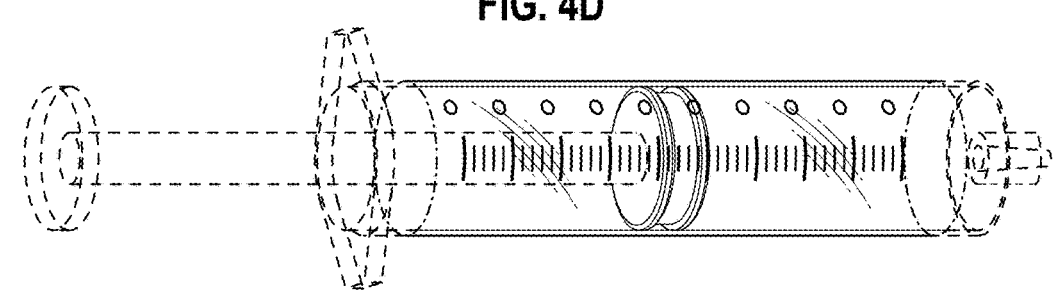
Figure 5A:
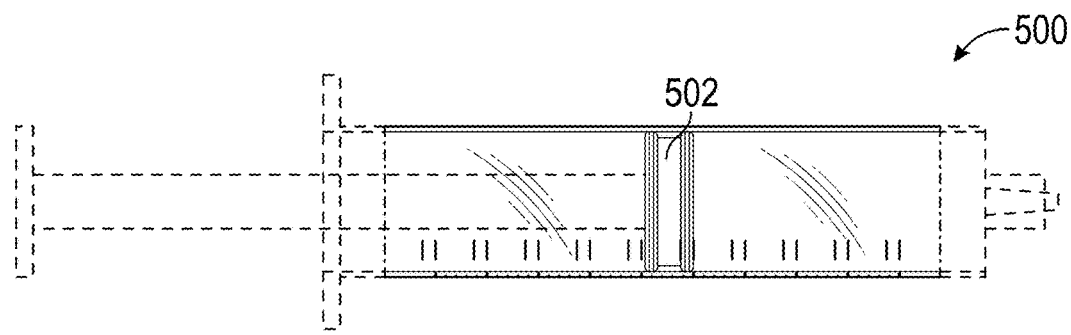
FIGS. 5A-5E illustrate pictorial representations of a syringe in accordance with an illustrative embodiment.
Figure 5B:
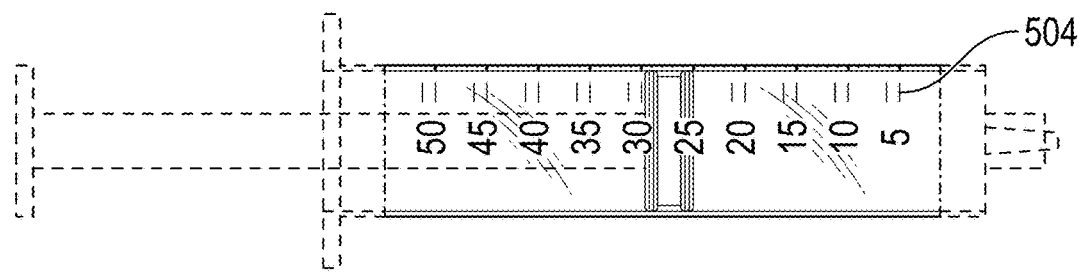
Figure 5C:
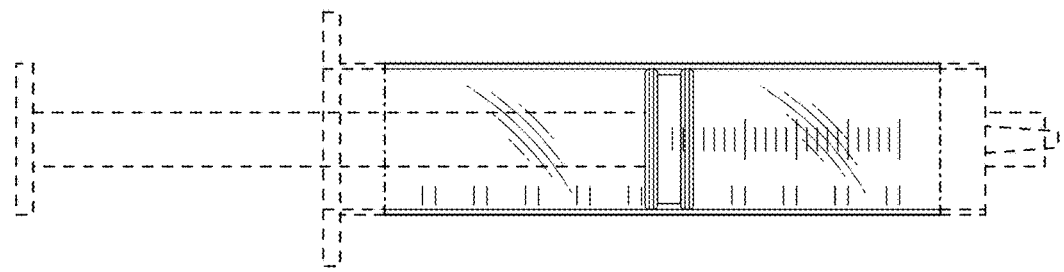
Figure 5D:
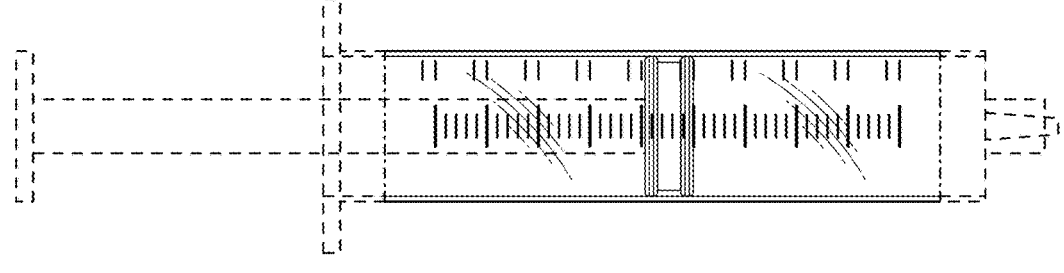
Figure 5E:
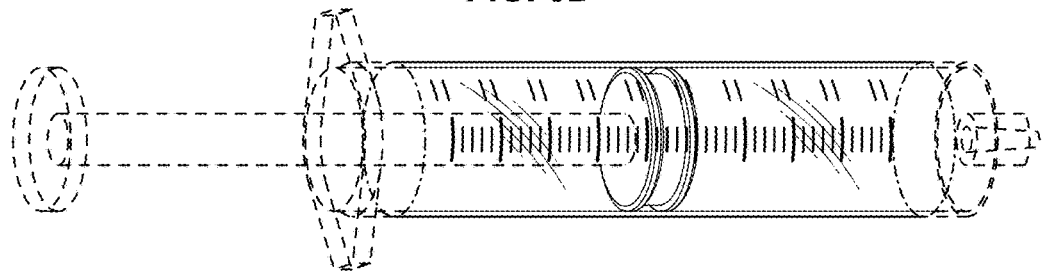

Turning now to FIGS. 2 and 3, FIG. 2 is a first side view of colored seals 200 and FIG. 3 is a perspective view of the colored seals 200 in accordance with an illustrative embodiment. In one embodiment, the colored seals 200 represent seals with bevels 202, and 204 (a double beveled seal). The colored seals 200 are shown as attached or integrated with a plunger 206. The bevels 202, 204 ensure that delivery agents are moved effectively within the barrel (not shown) based on the motion of the plunger 206 without residue, missed content, or waste. The motion of the plunger 206 may also be utilized to draw in delivery agents using suction or creation of a vacuum. As noted, the colored seals 200 may have any one or more bevels 202, 204 with most common seals having between 1-3 bevels 202, 204 (e.g., first bevel, second bevel, third bevel, etc.). However, the size, shape, and number of bevels 202, 204 may vary (e.g., the entire seal is a single/first bevel, no bevels, ten bevels, etc.). The width of the bevels 202 varies significantly between devices, syringes, or delivery devices (see for example the colored seals 100 of FIG. 1).

In one embodiment, the colored seals 200 include an opening or receptacle for receiving a first end 212 of the plunger 206. For example, the receptacle of the colored seal 200 may be fitted over the first end 212 of the plunger 206. A second end 214 of the plunger 206 is utilized to apply a delivery force (e.g., push, pull, application of force, etc.) whether applied by a user, robot, automated device, or so forth. For example, the colored seals 200 may be fitted over the first end 212 of the plunger 206 utilizing an interference fit. In other embodiments, connectors, linkages, or so forth may be utilized to connect the first end 212 of the plunger 206 to the colored seals 200. The colored seals 200 may also be attached utilizing adhesives, tapes, buttons, or other similar connection components. The plunger 206 may be solid or may be a framework or other structure.

FIGS. 4A-4E illustrate pictorial representations of a syringe 400 in accordance with an illustrative embodiment. The syringe 400 is slightly rotated in FIGS. 4A-4E to better show a colored seal 402, a barrel 404, a delivery end 406, a plunger 408, and other portions of the syringe 400 including barrel markings 410. In one embodiment, the barrel markings 410 may include fill indicators 412, volume lines 414, and measurement numbers 416. In various embodiments, the syringe 400 may utilize one or more of the barrel markings 410.

The volume lines 414 are markings or indicators that show the volume of delivery agent within the barrel 404 of the syringe 400 at the applicable volume line. The volume lines 414 are utilized to make careful and accurate measurements of the delivery agent. In one embodiment, main or key volume lines 414 may be associated with one or more fill indicators 412 to help the user determine that the desired volume of delivery agent is within the syringe 400. In one embodiment, the volume lines 414 may include differently colored markings or indicators for different common measurements for the syringe 400. For example, the syringe 400 may include 1 mL, 3 mL, 5 mL, 10 mL, or so forth. Specific units or markings may also be marked by the volume lines 414 or other markings.

The measurement numbers 416 are markings including alphanumeric characters (e.g., numbers, text, symbols, etc.) that further indicates the volume of the delivery agent in the syringe 400 at an associated volume line 414. In one embodiment, the measurement numbers 416 represent line shapes or hollow shapes (e.g., a line forming the exterior shape of the number with an open or transparent interior). As a result, the measurement numbers 416 may be more visible when the colored seal 402 is positioned at a point associated with the measurement number 416 (e.g., a specific volume or measurement).

The fill indicators 412 are demarcation points that indicate that the syringe 400 is filled to a specified level or measurement. In one embodiment, the position of the fill indicators 412 corresponds with the size and shape of the colored seal 402 and the barrel 404 such that when the colored seal 402 is visible within fill indicators 412 the desired measurement or volume has been reached. In some embodiments, the fill indicators 412 may be slightly offset from the barrel markings 410 to compensate for the size and shape of the colored seal 402 (e.g., arced ends, upper shape, etc.) and the exact volumes within the barrel 404 at each of the fill indicators 412. The utilization of the fill indicators 412 along with the colored seal 402 provides a unique visual presentation that when utilized in combination allows users to more clearly and accurately measure mixtures, compounds, medicines, or so forth. In some embodiments, accurate measurements can mean the difference between life-and-death, proper or improper treatment, accurate dosing (rather than overdosing or under dosing), and so forth.

In one embodiment, the size of the fill indicators 412 may correspond with the size of one or more bevels of the colored seal 402 when moved within the barrel 404. As is well known, the bevels appear to be larger when utilized within the barrel 404 because of the elastic properties of the colored seal as well as the friction and imparted forces. Various physical forces cause the bevels to appear larger within the barrels 404 due to friction, high/low pressures, compression, and so forth.

In one embodiment, the fill indicators 412 may represent shapes, such as the circles shown. Circles are beneficial because many users already associate filling a circle with completing a task or measurement. In another embodiment, the colored seal 402 may also include a fill indicator that may be fitted within the fill indicators 412 at the corresponding measurement levels. For example, the fill indicator of the barrel 404 may include a circle and the colored seal 402 may include a slightly smaller circle (e.g., a larger diameter for the fill indicator 412 of the barrel and a smaller diameter for the fill indicator of the colored seal 402) that fits exactly within the circle of the barrel 404 to reach an exact volume of delivery agent within the barrel 404. Various other complimentary shapes may also be utilized (e.g., circle and X, Square and plus sign, squares, etc.). Multiple fill indicators as described may be sized for accurate alignment, measurements, and utilization by the user. For example, circles aligned within circles may be utilized. In another embodiment, the syringe 400 may utilize a ring on the colored seal 402 that aligns with the fill indicator 412 that is also a ring. Other objects, shapes, patterns, or so forth may be utilized for the colored seal 402 and the barrel 404.

In one embodiment, the barrel markings 410 are black. In other embodiments, other colors (fluorescent or neon yellow, blue, orange, magenta, violet, green, pink, red, green, etc.) or combinations of colors may be utilized for the different portions of barrel markings 410. For example, the volumetric lines 414 and measurement text 416 may be in black (or first color) and the fill indicators 412 may be in a second color. As previously noted, the fill indicators 412 may represent a line shape or may include a fill color. In one embodiment, the line colors of the fill indicators 412 may be distinct from an associated fill color of the fill indicators 412. The fill color may be utilized to show a distinct color when the colored seal 402 is aligned with (or below) the fill indicator 412. For example, a bright yellow colored seal 402 with a blue fill indicator 412 may appear or otherwise present a green fill indicator 412 when the colored seal 402 is properly positioned within the barrel 404. Multiple color combinations may be utilized to provide fill indicators that are most visible and distinct to the user filling the syringe 400. Any number of different colored seals 402 may be utilized as defined by RGB code or HEX (e.g., #0047BD #07B9FC, #FFF735, #16DD36, #39FF14, #0052A5, #ccff00, #06A9FC, #681E7E, #FF0000, #FFFF00, #FF007F, etc.).

FIGS. 5A-5E illustrate pictorial representations of a syringe 500 in accordance with an illustrative embodiment. The syringe 500 illustrates colored seals 502 and fill indicators 504 shown as parallel line markings. As previously noted, the separation of the line markings may be associated with the width of the bevels of the colored seals 502. The fill indicators 504 are sized and positioned according to the measurement increments for the syringe 500. In some embodiments, the syringe 500 may only have limited markings for specific volumes of delivery agent (e.g., 5 mL, 20 mL, 100 mL, etc.). For example, particular applications may be associated with specific treatments, illnesses, or situations, such as anesthesia, antibiotics, immunizations, cancer treatments, autoimmune treatments, diabetes/insulin, fertility drugs, vitamins (e.g., vitamin B12), hormones, epinephrine, steroids, and other prescribed medications or injectables. As noted, the measurements and fill indicators may correspond to mL, cc, units, or any number of volume measurements.

Figure 6:
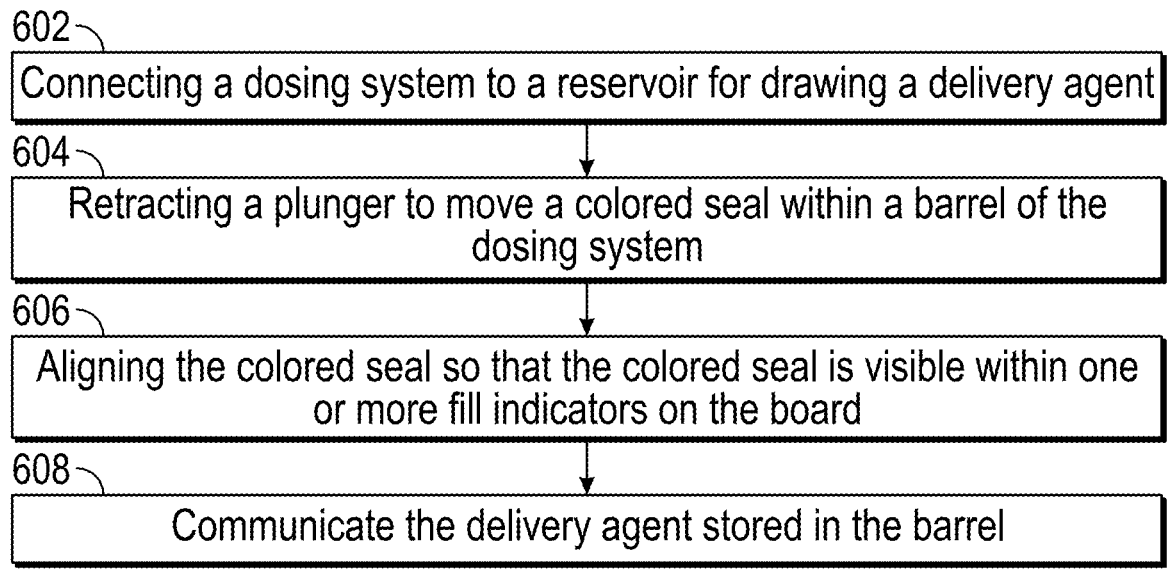
FIG. 6 is a flowchart of a process for filling a dosing system in accordance with an illustrative embodiment.

FIG. 6 is a flowchart of a process for filling a dosing system in accordance with an illustrative embodiment. The dosing system may be utilized by a user (e.g., individual, doctor, nurse, medical professional, technician, scientist, etc.), automated device, mechanical system, or so forth. The dosing system may represent a syringe, syringe system, dosing device, dosing system, or other delivery device utilizing a colored seal. The colored seal may be a single color or multi-colored. In one embodiment, the colored seals are fluorescent, neon, glow-in-the-dark, DayGlo, or other bright colors. However, muted or other distinct colors (e.g., pastels, primary, etc.) or patterns (e.g., layered, striped, checkered, random, etc.) may also be utilized.

In one embodiment, the process may begin by connecting a dosing system to a reservoir for drawing a delivery agent (step 602). The dosing system may be connected utilizing a needle, syringe, connector (e.g., Slip-Tips®, Luer-Lok®, Luer Slip, eccentric, catheter, permanently attached needle, screw-on, interlocking, etc.), tubing, or so forth. The reservoir may represent a vial, bottle, pouch, or so forth. The dosing system may utilize a tube shaped or cylindrical barrel as are known in the art. Alternatively, the barrel may be oval shaped, square, or other shapes with the colored seal being similarly shaped to provide an air tight seal. The various components of the syringe may be removed from sterile containers or a sterilizing device as part of the process of FIG. 6. In addition, any number of sterile techniques may be utilized as is known in the art (e.g., washed/gloved hands, protective equipment or clothing, alcohol swabs, sterilized/clean environments, etc.).

Next, the user retracts a plunger to move a colored seal within a barrel of the dosing system (step 604). The plunger may be permanently or temporarily attached to colored seal by the user or during a manufacturing process. The barrel may include barrel markings that may include line markings, numeric markings, and fill indicators. In one embodiment, the barrel markings may be printed, inked, deposited, engraved, or otherwise marked. The barrel markings may be black or may represent any number of other colors. In one embodiment, the fill indicators may correspond to numeric markings on the barrel (e.g., 0.5 mL, 1 mL, 5 mL, 10 ml, 50 mL, 100 mL, etc.). The numeric, textual, or other markings may utilize any number of fonts (e.g., solid, hollow, different/distinct colors, etc.). The fill indicators may be exactly positioned on the barrel for filling the barrel to exact volumetric levels. The fill indicators may be positioned to exact measurements, filling, and dosing associated with the size and shape of the colored seal and the barrel. As is commonly the case, the barrel is transparent, semi-transparent, clear, see-through, or otherwise allows the colored seal to be seen through the barrel.

Next, the user aligns the colored seal so that the colored seal is visible within one or more fill indicators on the barrel (step 606). In one embodiment, the size of the fill indicators may correspond to a width of a first bevel on the front edge (e.g., facing a delivery end of the syringe—needle end) of the colored seal when positioned within the barrel. For example, the width of the first bevel may completely visually fill the fill indicator when properly aligned. In one embodiment, the numeric markings may also be hollow or represent line representations, such that the color of the colored seal are visible through the numeric markings. The numeric markings may also be aligned for accurate measurements. The delivery agent may be measured to the widest portion of the colored seal proximate the delivery agent. For example, this point is often a bevel or seal portion of the colored seal.

Next, the user communicates the delivery agent stored in the barrel (step 608). The delivery agent may be delivered through a delivery end of the barrel. The delivery end may be associated with a needle, tube, connector, or so forth. For example, the delivery agent may be injected into a receiving party. The delivery agent may be pushed or ejected from the barrel through any number of delivery ends, connectors, or mechanisms. The fill indicators allow for the exact filling and delivery of the delivery agent. As a result, delivery agents are more accurately communicated, measured, or allocated. In some embodiments, the user may communicate a portion of the delivery agent within the barrel of the syringe by using the fill indicators to more accurately measure the desired portion.

The fluorescent colored seals are much easier to read than traditional black-on-black measurement systems. The fill indicators and other barrel markings (e.g., measurement markings, numeric markings, etc.) show up so much more clearly against the background of the colored seal. As a result, users with visual or cognitive limitations may more effectively perform measurements particularly where self-dosing or measurements are required.

Figure 7:
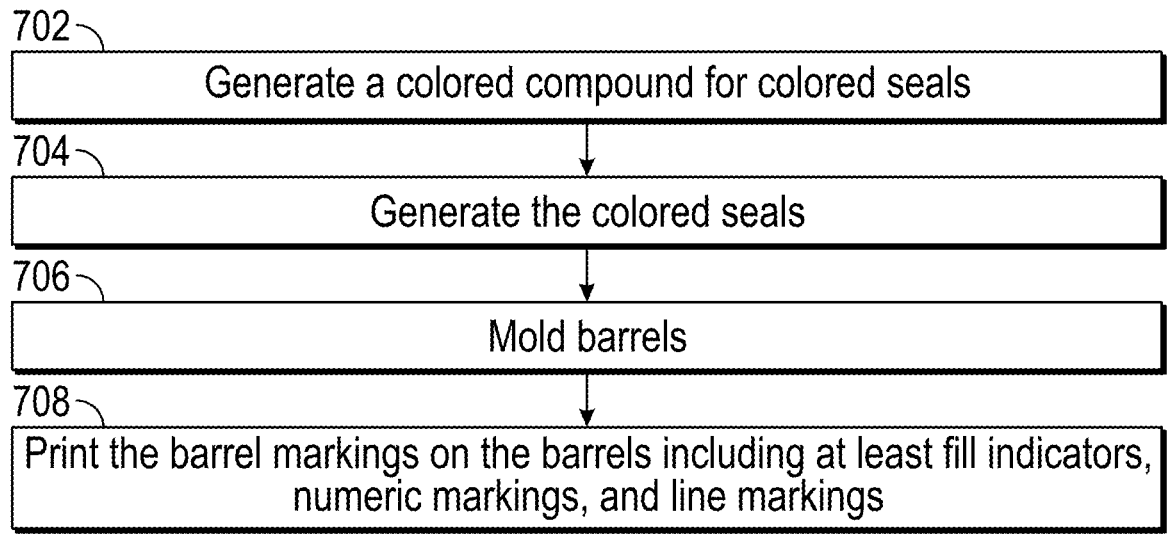
FIG. 7 is a flowchart of a process for manufacturing colored seals in accordance with an illustrative embodiment.

FIG. 7 is a flowchart of a process for manufacturing colored seals in accordance with an illustrative embodiment. The process may begin by generating a colored compound for colored seals (step 702). The compound may represent a rubber, plastic, polymer, or other compound. Any number of dyes, pigments, toners, dispersions, inks, bases, paints, coatings, color compounds, or other compounds, additives, or mixtures may be utilized to provide the unique colors utilized by the colored seals.

Regular dyes, utilized for black seals, absorb ultra violet light along with all the other wavelengths not reflected. The fluorescent, neon, bright or other dyes, compounds, and materials utilized for the colored seals may respond to ultra violet light or other spectra. The molecules of the fluorescent dyes are excited (from a ground state) by ultra violet energy and other visible spectrum and afterwards as the energy level within the molecules decreases (from an excited state), the molecules release the excess energy as visible light. For example, fluorescent dyes turn ultra violet light/energy into visible light and as a result the colored seals are more effectively viewed. Fluorescent colors use a larger amount of both the visible spectrum and the lower wavelengths compared to conventional colors. The colors of the colored seals not only absorb and convert light energy of the dominant wavelength, but also the wavelengths of ultraviolet rays and other colors lower in the visible spectrum. As a result, the user's eyes perceives a far more intense color. In one example, a conventional color is able to reflect a maximum of 90% of a color present in the spectrum whereas a fluorescent color can reflect as much as 200% to 300%. In one embodiment, the brightest, most visible color to a user may be a fluorescent yellow-green. Some studies have shown that human eyes are built to be most sensitive to that particular wavelength of light (550 nanometers) during daylight conditions.

Next, the system generates the colored seals (step 704). The colored seals may be generated utilizing injection molding methods, three-dimensional printing, and so forth. The colored seals may be coated with one or more coatings or reagents. The colored seals may utilize an ultrapure rubber or composite formulation to prevent contamination and minimizing extractables. The colored seals and other components of the syringes or dosing systems may be manually or automatically accepted utilizing vision systems or optics.

Next, the system molds barrels (step 706). As previously noted, the barrels may be formed from plastic, glass, or other materials that are transparent, semi-transparent, or otherwise see-through.

Next, the system prints the barrel markings on the barrels including at least fill indicators, numeric markings, and line markings (step 708). In some embodiments, ink is rolled onto the barrel to print the barrel markings. In other embodiments, laser deposition of ink may be utilized. Any number of digital or Litho presses may be utilized. In other embodiments, the fill indicators, numeric markings, and line markings may be printed as stand-alone markings or in unique combinations (e.g., fill indicators and numeric markings only, fill indicators including numbers with line markings, etc.). In some embodiment, the syringe may include a safety mechanism, such as clamp, cover, or retracting feature for the needles of the syringe.

The various manufacturing and printing processes may also utilize chemical vapor deposition, physical vapor deposition, electrostatic deposition, atomization, sprays, and so forth to generate the colored seals, specialized barrels and markings, or other components. Gas or liquid baths may also be utilized to apply different anti-bacterial, anti-fungal, hydrophobic, sterilized, or other layers.

Figure 8:
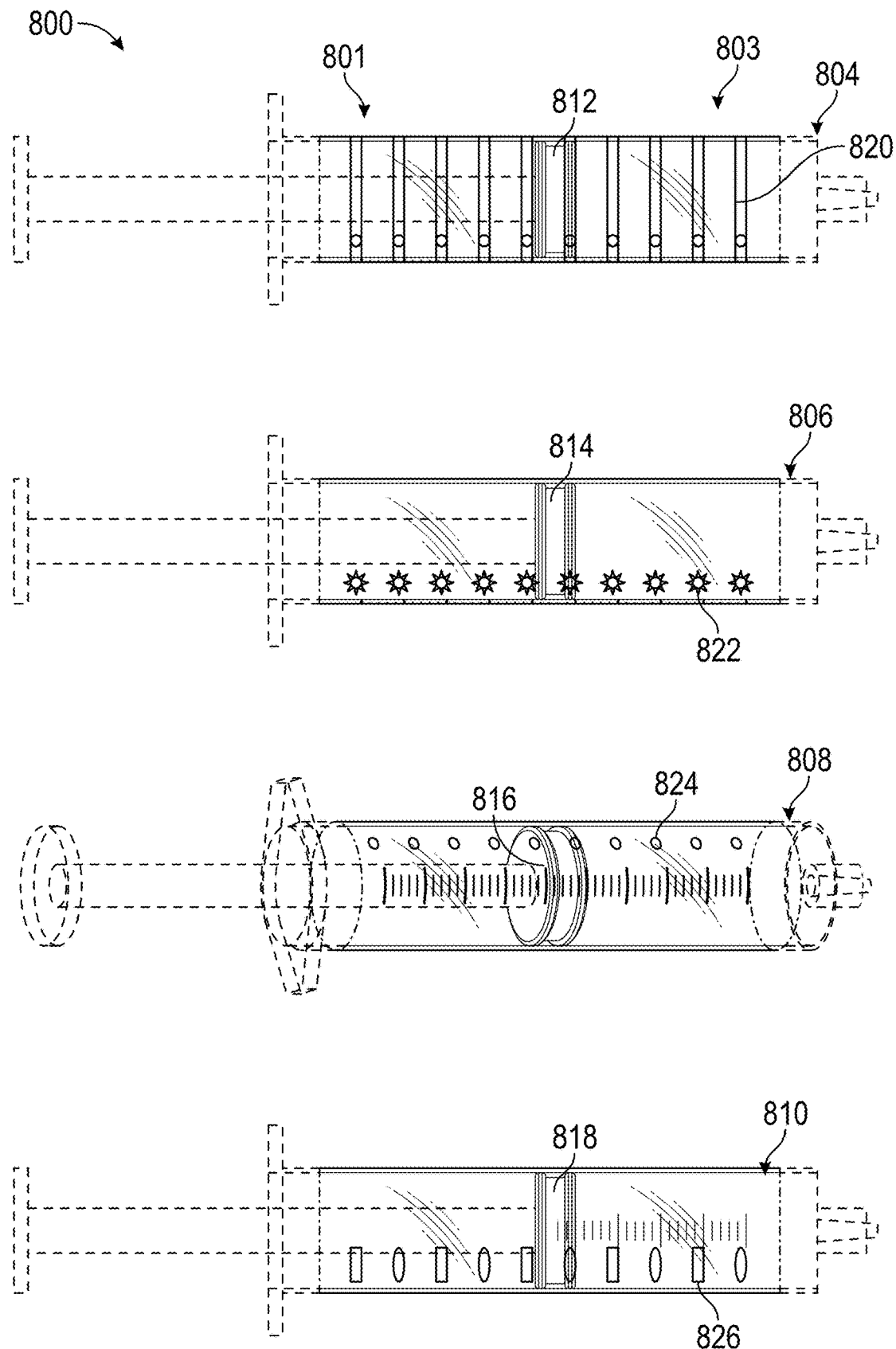
FIG. 8 is a pictorial of syringes with colored seals and fill indicators in accordance with an illustrative embodiment.

FIG. 8 is a pictorial of syringes 800 with colored seals 801 and fill indicators 803 in accordance with an illustrative embodiment. The syringes 800 include syringes 804, 806, 808, and 810 (jointly syringes 800) with colored seals 812, 814, 816, and 818 (jointly colored seals 801) and fill indicators 820, 822, 824, and 826.

The colored seals 812, 814, 816, and 818 show various fluorescent or neon colors, such as yellow, orange, blue, and red/pink. The colored seals 801 may also utilize any number of similar color variations as disclosed herein known for their brightness and distinctiveness to the human eye. The colored seals 801 may also utilize materials, coatings, paint, or so forth that become luminescent, distinct, or more visible in specified spectrums (e.g., natural light, ultraviolet lights, etc.) for various medical purposes. The syringes 800 may be utilized with any number of specific light emitting devices or systems.

The syringe 804 may utilize fill indicators 820. The fill indicators may include bands that correspond to the size and shape of the bevels of the colored seal 812. As a result, a user may be able to more accurately draw a specified amount of medicine, fluid, or delivery agent. For example, a first or front bevel of the seal may be aligned with a desired one of the fill indicators 820. The bevel may represent a portion (e.g., segment, sidewalls, contact points, bands, extensions, etc.) of the colored seal 812 that contacts the sides or surfaces of the syringe 804. Although not shown, the fill indicators may be labeled with a specified volumetric measurement (e.g., 1 mL, 5 mL, 1 tsp, 1 Tbsp, etc.) in any number of languages and measurement standards. In one embodiment, the fill indicators 820 may also include circles or other shapes as shown.

The fill indicators 822 of syringe 806 may represent shapes that are distinctive and noticeable to a user, such as a star. All or portions of the shapes used as fill indicators 814 may correspond to the size and shapes of the colored seal 814 within the barrel of the syringe 806.

As shown the syringe 808 may include fill indicators 824 with measurement lines that are aligned with the fill indicators 824 for measuring exact amounts of fluid. For example, the fill indictors 824 may be positioned on the barrel, such that one of multiple major measurement points is reached when the colored seal 816 is visible with the corresponding fill indicator 824 (e.g., 5 mL, 10 mL, 15 mL, etc.). The fill indicators 824 and associated measurement lines and numeric markings may be positioned based on the size, shape, discharge dynamics (e.g., fluid that is not ejected, syringe length, nozzle type, etc.) so that exact quantities of delivery agent may be discharged from the syringe 808.

The syringe 810 shows the colored seal 818 utilized with differently shaped fill indicators 826. In some embodiments, the different fill indicators may be associated with different fill levels. In some embodiments, each major measurement value may have a differently shaped, colored, or configured fill indicator 826 for medical professionals to give exact instructions and details for preparing the syringe 810 and delivering the necessary delivery agents.

The illustrative embodiments are not to be limited to the particular embodiments and examples described herein. In particular, the illustrative embodiments contemplate numerous variations in the type of ways in which embodiments may be applied to syringes, syringe systems, barrel and colored seal systems, or so forth. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes or methods of the invention. It is understood that any other modifications, substitutions, and/or additions may be made, which are within the intended spirit and scope of the disclosure. For the foregoing, it can be seen that the disclosure accomplishes at least all of the intended objectives.

The previous detailed description is of a small number of embodiments for implementing the invention and is not intended to be limiting in scope. The following claims set forth a number of the embodiments disclosed with greater particularity.

What is claimed is:

1. A colored seal system, comprising:
a barrel including a delivery end and an open end, the barrel including a plurality of barrel markings, wherein the barrel markings include at least line markings, numeric markings, and a plurality of fill indicators, wherein the plurality of fill indicators define open space enclosed within the plurality of fill indicators, and wherein at least one of the plurality of fill indicators is aligned with at least one of the numeric markings; and
a colored seal slidably positioned within the barrel for moving a delivery agent, wherein the colored seal is visible within the open space of at least one of the plurality of fill indicators.

2. The colored seal system of claim 1, wherein the colored seal is connected to a plunger for moving the colored seal within the barrel to insert and remove the delivery agent.

3. The colored seal system of claim 1, wherein the barrel is transparent or semi-transparent, and wherein the colored seal is at least one of a fluorescent, neon, or glow-in-the-dark.

4. The colored seal system of claim 1, wherein the plurality of fill indicators have a color distinct from the colored seal.

5. The colored seal system of claim 4, wherein the colored seal includes a plurality of bevels, and wherein the plurality of bevels are a distinct color from other portions of the colored seal.

6. The colored seal system of claim 1, wherein the plurality of fill indicators are hollow shapes.

7. The colored seal system of claim 6, wherein the plurality of fill indicators are circles.

8. The colored seal system of claim 1, wherein the plurality of fill indicators are one or more of a square, triangle, oval, star, octagon, hexagon, and rectangle.

9. The colored seal system of claim 1, wherein a size of a first bevel of the colored seal within the barrel corresponds to a size of the plurality of fill indicators.

10. The colored seal system of claim 1, wherein the measurements for the delivery agent are associated with a position of the plurality of fill indicators to compensate for the size and shape of the colored seal.

11. The colored seal system of claim 1, wherein a front end of the colored seal is aligned with one of the plurality of fill indicators such that a color of the colored seal is visible within the fill indicator, and wherein one of the plurality of fill indicators is associated with one of the measurements.

12. The colored seal system of claim 1, wherein the plurality of fill indicators represent a pair of lines extending all or a portion of a circumference of the barrel.

13. The colored seal system of claim 12, wherein a separation of the pair of lines is associated with a width of a bevel of the colored seal within the barrel.

14. The colored seal system of claim 1, wherein the plurality of fill indicators are filled with a second color.

15. The colored seal system of claim 14, wherein a new color is visible within the open space when the colored seal is aligned with the second color of the plurality of fill indicators.

16. The colored seal system of claim 1, wherein the barrel markings are black.

17. The colored seal system of claim 1, wherein the barrel markings are printed on the barrel.

18. The colored seal system of claim 1, wherein the delivery end of the barrel includes one of a needle, a connector, or a tube.

19. The colored seal system of claim 1, wherein the colored seal system is a syringe, a syringe system, a dosing system, a dosing device, or a syringe device.

20. The colored seal system of claim 1, wherein the delivery agent is a liquid or solid.

21. The colored seal system of claim 1, further comprising:
    an actuator configured to automatically move the colored seal within the barrel to deliver the delivery agent.

22. The colored seal system of claim 1, wherein the plurality of fill indicators are utilized to fill the barrel to a desired level.

23. A syringe, comprising:
    a barrel including a needle at a first end, the barrel including a plurality of barrel markings, wherein the barrel markings include at least line markings, numeric markings, and a plurality of fill indicators, wherein the plurality of fill indicators define open space enclosed within the plurality of fill indicators, and wherein at least one of the plurality of fill indicators is aligned with at least one of the numeric markings; and
    a colored seal slidably positioned within the barrel for moving a delivery agent within the barrel, wherein the colored seal is fluorescent, and wherein the colored seal is visible within the open space of at least one of the plurality of fill indicators.

24. A dosing system, comprising:
    a barrel including a delivery end and a plunger end, wherein the barrel includes barrel markings, the barrel markings include at least measurements including line markings and volumetric markings and one or more fill indicators aligned with at least one or more of the volumetric markings, the fill indicators define open space enclosed within the fill indicators;
    a colored seal slidably secured within the barrel for communicating a delivery agent within the barrel, wherein the colored seal is fluorescent, and wherein the colored seal is visible within the open space of at least one of the fill indicators when aligned; and
    a plunger connected to the colored seal for receiving a user force to add the delivery agent to or eject the delivery agent from the barrel.

* * * * *